United States Patent [19]

Arai et al.

[11] Patent Number: 5,856,202

[45] Date of Patent: Jan. 5, 1999

[54] METHOD FOR DETERMINING ANTISTREPTOLYSIN O ANTIBODY

[75] Inventors: Kenji Arai, Shizuoka-ken; Yoshitaka Kagimoto, Mishima, both of Japan

[73] Assignee: Asahi Kasei Kogyo Kabushiki Kaisha, Osaka, Japan

[21] Appl. No.: 558,455

[22] Filed: Nov. 9, 1995

[30] Foreign Application Priority Data

Nov. 15, 1994 [JP] Japan ..................................... 6-280663

[51] Int. Cl.⁶ ................................................. G01N 33/543
[52] U.S. Cl. .......................... 436/518; 436/523; 436/524; 436/528; 436/532; 436/533; 436/522; 424/165.1
[58] Field of Search .......................... 424/165.1; 436/518, 436/523, 524, 528, 533, 532; 435/7.34

[56] References Cited

FOREIGN PATENT DOCUMENTS

| 0 268 773 | 6/1988 | European Pat. Off. . |
| 0 478 786 | 3/1992 | European Pat. Off. . |
| 55-31960 | 3/1980 | Japan . |
| 63-117265 | 5/1988 | Japan . |

OTHER PUBLICATIONS

R. Lancefield, "A serological differentiation of Human and Other Groups of Hemolytic Streptococci", J. Exp. Med., 1933, vol. 57, pp. 571–593.

D. Prigent et al., "Interaction of Streptolysin O with Sterols", Biochimica et Biophysica Acta, 1976, vol. 443, pp. 288–300.

T. Nagata, "Disease caused by Infection with Hemolytic Streptococcus", Rinsho–kensa (Laboratory Examinations), 1979, vol. 23, pp. 1172–1175. Translated sections only.

L. Rantz et al., "A Modification of the Technic for Determination of the Antistreptolysin Titer", Proc. soc. Exp. Biol. Med., 1945, vol. 59, pp. 22–25.

E. Edwards, "Protocol for Micro Antistreptolysin O Determinations", J. Bacteriol., 1964, vol. 87, pp. 1254–1255.

H. Fujimoto et al., "Antistreptolysin O", Rinsho–byori (Clinical Pathology), 1992, vol. 40, pp. 21–27. Eng Abst. only.

T. Miura et al., Eisei–kensa (Hygienic Examinations), 1987, vol. 36, pp. 36–40. Translated sections only.

*Primary Examiner*—James C. Housel
*Assistant Examiner*—Rosemary Ashton
*Attorney, Agent, or Firm*—Young & Thompson

[57] ABSTRACT

A method for immunologically determining antistreptolysin O antibody comprises contacting a test sample solution containing antistreptolysin O antibody with a binding agent to selectively bind the antistreptolysin O antibody to the binding agent, and determining an amount of the bound antistreptolysin O antibody, wherein the binding agent comprises a streptolysin O-immobilized carrier obtained by contacting a solution containing streptolysin O with a carrier having immobilized thereon at least one steroid represented by formula (1):

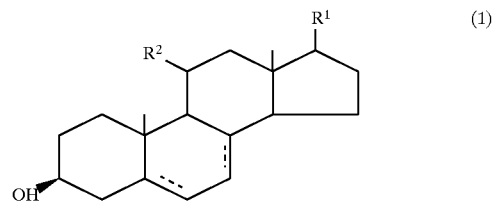

wherein $R^1$ is a side chain moiety of cholesterol or a side chain moiety of cholic acid, wherein each of the side chain moieties is independently unsubstituted or substituted and independently saturated or unsaturated; $R^2$ is hydrogen or hydroxyl; and each dashed line independently represents a single bond or no bond. The method of the present invention can be used for determining antistreptolysin O antibody specifically, accurately and easily and can be practiced not only by manual operation but also by automated operation.

8 Claims, 6 Drawing Sheets

FIG.1

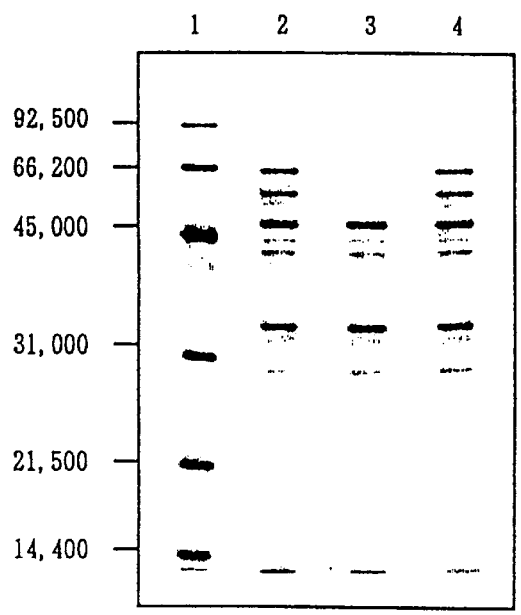

Lane 1: Separation pattern of molecular weight marker

Lane 2: Separation pattern of proteins contained in the original sample solution containing streptolysin O Lane 3: Separation pattern of proteins contained in the solution recovered from the cholesterol-immobilized microtiter plate Lane 4: Separation pattern of proteins contained in the solution recovered from the microtiter plate having no cholesterol immobilized thereon T-shaped portion at the forward end of each bar represents a range of error Antistreptolysin O antibody titer (IU/ml)

Antistreptolysin O antibody titer determined
by Rantz-Randall method (Todd Unit)

Antistreptolysin O antibody titer (IU/ml)

METHOD FOR DETERMINING ANTISTREPTOLYSIN O ANTIBODY

BACKGROUND OF THE INVENTION

1. Field of The Invention

The present invention relates to a method for determining antistreptolysin O antibody. More particularly, the present invention is concerned with a method for immunologically determining antistreptolysin O antibody, which comprises contacting a test sample solution containing antistreptolysin O antibody with a binding agent capable of specifically binding the antistreptolysin O antibody thereto, thereby selectively binding the antistreptolysin O antibody to the binding agent by antigen-antibody reaction, and determining an amount of the antistreptolysin O antibody bound to the binding agent, wherein the binding agent comprises a streptolysin O-immobilized carrier obtained by contacting a solution containing streptolysin O with a carrier having immobilized thereon at least one specific steroid. The binding agent to be used in the method of the present invention is capable of specifically binding the antistreptolysin O antibody thereto, so that the determination of antistreptolysin O antibody can be readily conducted with high specificity and accuracy. Further, the method of the present invention need not use erythrocytes, which are unstable and have different qualities depending on the lot of erythrocytes. Due to the above-mentioned advantages, the method of the present invention enables automation of specific and accurate determination of the antistreptolysin O antibody, differing from conventional determination methods which cannot be employed to automate specific or accurate determination of the antistreptolysin O antibody. The method of the present invention can be advantageously used for the diagnosis of infection with group A hemolytic *streptococci*.

2. Description of Related Art

Antistreptolysin O antibody is an antibody against streptolysin O. Streptolysin O is a toxin (which is a member of the group of thiol-activated bacterial cytolysins) produced, for example, by group A hemolytic *streptococci* classified according to the serological classification by Lancefield (see Lancefield, R. C., J. Exp. Med., Vol. 57, pp.571–595, 1933), and is generally known as a protein having a molecular weight in the range of from 50,000 to 70,000. Streptolysin O is known to interact with cholesterol and related sterols (see Prigent, D. et al., BBA, Vol. 443, pp.288–300, 1976), and exert cytolytic effects on a broad range of mammalian cells. Streptolysin O lyses erythrocytes, usually under reductive conditions, e.g. in the presence of mercaptoethanol, by an interaction with membrane cholesterol. It is known that antistreptolysin O antibody level is elevated in the serum from a patient infected with group A hemolytic *streptococci*.

Group A hemolytic *streptococci* are pathogenic microorganisms which are causative of various diseases including tonsillitis, pharyngitis, skin purulence and scarlet fever, and secondary diseases, such as rheumatic fever, glomerulonephritis, and the like. Most of these diseases manifest no specific clinical symptoms from which pathogenic microorganisms causing the diseases can be identified and, therefore, for clinical diagnosis of infections with group A hemolytic *streptococci*, confirmation of the presence of antistreptolysin O antibody and determination of the antibody titer have generally been utilized [see Tomika Nagata, "Rinshokensa (Laboratory Examinations)", Vol.23, Supplementary Edition, pp.1172–1175, 1979].

As methods for the determination of antistreptolysin O titer, the Rantz-Randall method using rabbit erythrocytes, sheep erythrocytes or human type O erythrocytes (see L. A. Rantz et al., Proc. Soc. Exp. Biol. Med., Vol.59, pp.22–25, 1945), and a modification of the Rantz-Randall method, i.e., the microtiter method (see Edwards, E. A.; J. Bacteriol., Vol.87, pp.1254–1255, 1964) have conventionally been widely used in routine assays. Both determination methods are based on the principle that antistreptolysin O antibody in a test sample solution neutralizes the hemolytic activity of streptolysin O.

Group A hemolytic *streptococci*, which have infected living bodies, produce not only streptolysin O, but also various other antigens, such as erythrogenic toxin, streptokinase, streptodornase, hyaluronidase, ribonuclease and neuraminidase and, in addition, various antibodies against these antigens occur in the blood [see "Rensakyukin-kansensho II: Sono Kiso-to-Rinsho (Streptococcicosis, Volume II: the basic and clinical)"; edited by Yuichi Shiokawa, Morimasa Yoshioka and Shigeyuki Hamada; pp.317–359, Hirokawa Shoten K. K., Japan, Jun. 25, 1992]. However, since the above determination methods utilize the hemolytic activity characteristic of streptolysin O, streptolysin O to be used as a reagent for the above determination methods need not necessarily be a purified one, and in the above determination methods, non-purified streptolysin O can be used for specifically recognizing and determining only antibody against streptolysin O, i.e. antistreptolysin O antibody, among antibodies against a number of antigens [Fujimoto et al., "Rinsho-byori (Clinical Pathology)", Vol.40, pp.21–27, 1992].

However, these determination methods require the use of fresh erythrocytes. Erythrocytes are unstable and different in quality between different lots, so that these determination methods using erythrocytes are likely to be unstable. Further, these determination methods necessarily involve complicated operations. Therefore, it is very difficult to automate these determination methods (see European Patent Application Publication No. 0 475 786 A2 corresponding to Unexamined Japanese Patent Application Laid-Open Specification No. Hei 6-186233).

In recent years, a determination method for antistreptolysin O antibody titer which is based on the principle of immunoagglutination and uses a carrier (such as colloidal latex particles) having streptolysin O immobilized thereon, has been used [see T. Miura et al., "Eisei-kensa (Hygienic Examinations)", Vol.36, pp.36–40, 1987]. This conventional determination method using a streptolysin O-immobilized carrier is improved in that unstable erythrocytes need not be used and that this method can be automated, thus differing from the above-mentioned conventional determination methods utilizing as a criterion the hemolytic activity of streptolysin O.

However, the conventional determination method using a streptolysin O-immobilized carrier has the following disadvantages. Streptolysin O is generally prepared from a culture mixture of group A hemolytic *streptococci*. It is very difficult to obtain a highly purified streptolysin O from such a culture mixture, so that streptolysin O obtained from such a culture mixture of group A hemolytic *streptococci* usually contains a wide variety of other antigens produced by group A hemolytic *streptococci*. Therefore, when such streptolysin O is immobilized on a carrier, other antigens produced by group A hemolytic *streptococci* are also immobilized on the carrier together with the streptolysin O. Thus, the antibody titer which can be obtained by the conventional determination method using the above-mentioned streptolysin O-immobilized carrier is one which is obtained with respect to all antibodies which react with the various antigens immobilized on the carrier. Therefore, this conventional determination method using a streptolysin O-immobilized carrier has a problem in that it is unsatisfactory in reaction specificity to antistreptolysin O antibody [see Fujimoto et al., "Rinsho-byori (Clinical Pathology)", Vol.40, pp.21–27, 1992].

In these situations, it has been desired to develop a determination method which solves the problems accompanying the conventional methods for the determination of antistreptolysin O antibody. That is, it has been desired to develop a method for the determination of antistreptolysin O antibody, which can be used for accurately, easily determining antistreptolysin O antibody with high reaction specificity, and which can be performed by automated operation as well as by manual operation.

SUMMARY OF THE INVENTION

The present inventors have made extensive and intensive studies with a view toward solving the above-mentioned problems of the prior art. As a result, they have unexpectedly found that by contacting a solution containing streptolysin O with a carrier having physically or chemically immobilized thereon at least one steroid represented by formula (1):

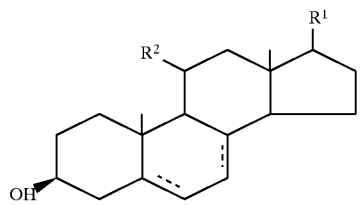

wherein $R^1$ is selected from the group consisting of a side chain moiety of cholesterol and a side chain moiety of cholic acid, wherein each of the side chain moieties is independently unsubstituted or substituted and independently saturated or unsaturated; $R^2$ is hydrogen or hydroxyl; and each dashed line independently represents a single bond or no bond, such that each dashed line and a solid line adjacent thereto together independently form a double bond or a single bond,
only the streptolysin O in the solution can be selectively immobilized on the carrier, thereby obtaining a streptolysin O-immobilized carrier, and that the immobilized streptolysin O still has the capacity of reacting to antistreptolysin O antibody and is capable of specifically binding antistreptolysin O antibody thereto. They have also found that by using the above streptolysin O-immobilized carrier, the specific determination of antistreptolysin O antibody can be conducted accurately and easily. The present invention has been completed, based on the above findings.

Accordingly, it is a primary object of the present invention to provide a method for immunologically determining antistreptolysin O antibody, which can be used to determine antistreptolysin O antibody specifically, accurately and easily and can be performed not only by manual operation but also by automated operation.

The foregoing and other objects, features and advantages of the present invention will be apparent to those skilled in the art from the following description and appended claims taken in connection with the accompanying drawings.

BRIEF DESCRIPTION OF THE DRAWINGS

In the accompanying drawings:

FIG. 1 shows electrophoresis patterns obtained in Example 1, including a pattern (lane 3) obtained by subjecting to SDS-polyacrylamide gel electrophoresis a reaction mixture which is obtained by contacting a solution containing streptolysin O with a carrier having cholesterol immobilized thereon;

DETAILED DESCRIPTION OF THE INVENTION

Figure 2:
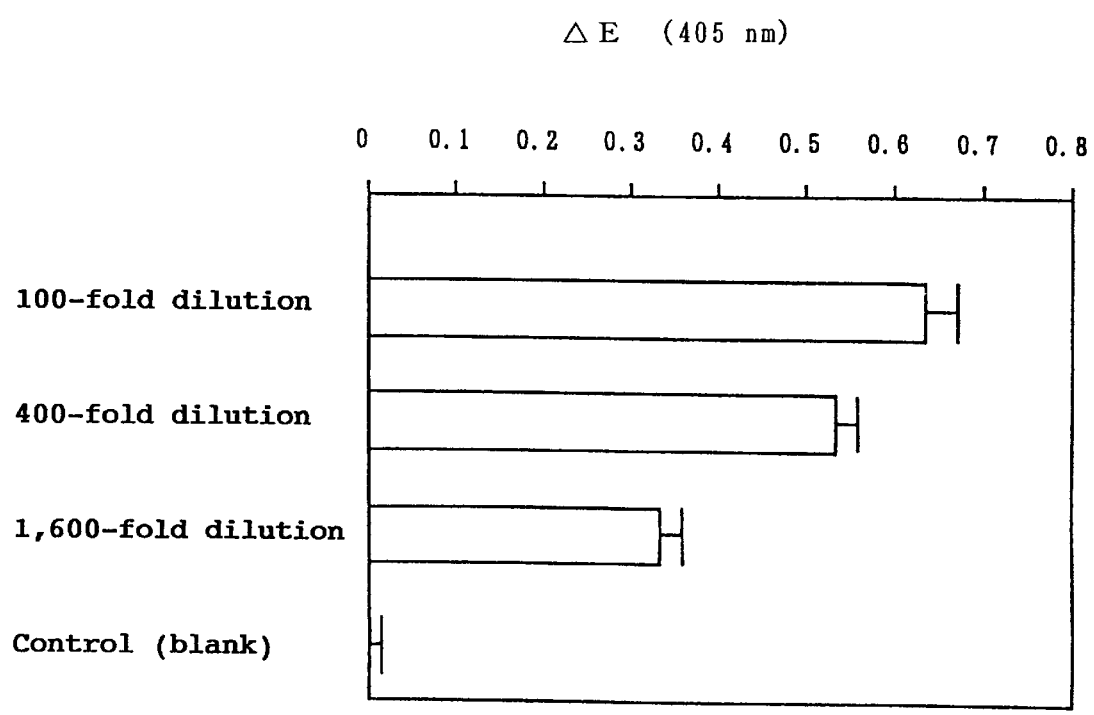
FIG. 2 is a graph showing the results of a test conducted in Example 2 for detecting an immune complex of immobilized streptolysin O with antistreptolysin O antibody.

Essentially, according to the present invention, there is provided a method for immunologically determining antistreptolysin O antibody, which comprises:

(a) contacting a test sample solution containing antistreptolysin O antibody with a binding agent capable of specifically binding the antistreptolysin O antibody thereto, thereby selectively binding the antistreptolysin O antibody to the binding agent by antigen-antibody reaction, and (b) determining an amount of the antistreptolysin O antibody bound to the binding agent, the binding agent comprising a streptolysin O-immobilized carrier obtained by contacting a solution containing streptolysin O with a carrier having immobilized thereon at least one steroid represented by formula (1):

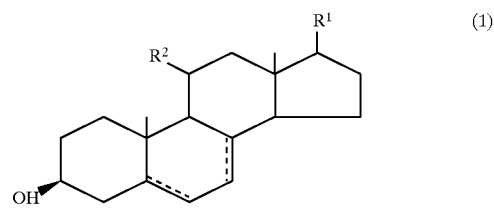

wherein $R^1$ is selected from the group consisting of a side chain moiety of cholesterol and a side chain moiety of cholic acid, wherein each of the side chain moieties is independently unsubstituted or substituted and independently saturated or unsaturated; $R^2$ is hydrogen or hydroxyl; and each dashed line independently represents a single bond or no bond, such that each dashed line and a solid line adjacent thereto together independently form a double bond or a single bond.

In $R^1$ of formula (1), which is selected from the group consisting of a side chain moiety of cholesterol and a side chain moiety of cholic acid, each of the side chain moieties is independently unsubstituted or substituted with hydroxyl, a lower alkyl having 1 to 4 carbon atoms, preferably 1 to 2 carbon atoms, or a lower acyl having 2 to 4 carbon atoms, preferably 2 to 3 carbon atoms and independently saturated or unsaturated with one or two double bonds.

A specific example of such a side chain moiety of cholesterol is a group represented by formula (2):

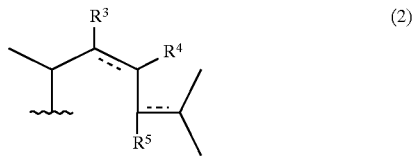

(2)

wherein $R^3$ represents hydrogen, hydroxyl, a lower alkyl having 1 to 4 carbon atoms, preferably 1 to 2 carbon atoms, or a lower acyl having 2 to 4 carbon atoms, preferably 2 to 3 carbon atoms; $R^4$ represents hydrogen, hydroxyl, a lower alkyl having 1 to 4 carbon atoms, preferably 1 to 2 carbon atoms, or a lower acyl having 2 to 4 carbon atoms, preferably 2 to 3 carbon atoms; $R^5$ represents hydrogen, hydroxyl, a lower alkyl having 1 to 4 carbon atoms, preferably 1 to 2 carbon atoms, or a lower acyl having 2 to 4 carbon atoms, preferably 2 to 3 carbon atoms; and each dashed line independently represents a single bond or no bond, such that each dashed line and a solid line adjacent thereto together independently form a double bond or a single bond.

In preferred examples of such a group of formula (2), each of $R^3$ and $R^4$ is hydrogen, and $R^5$ is hydrogen, hydroxyl, methyl or ethyl. Specific preferred examples of groups of formula (2) include the corresponding side chain moieties of cholesterol, β-sitosterol, stigmasterol, campesterol, ergosterol, cerebrosterol, and desmosterol.

A specific example of such a side chain moiety of cholic acid is a group represented by formula (3):

(3)

wherein the dashed line represents a single bond or no bond, such that the dashed line and the solid line adjacent thereto together form a double bond or a single bond.

Specific examples of steroids represented by formula (1) include cholesterol, 7-dehydrocholesterol, cholestanol, coprostanol, $\Delta^7$-cholestenol, $\Delta^7$-coprostenol, β-sitosterol, 7-dehydro-β-sitosterol, stigmasterol, 7-dehydrostigmasterol, campesterol, 7-dehydrocampesterol, stigmastanol, $\Delta^7$-stigmastenol, 11α-hydroxycholesterol, $\Delta^{22}$-stigmastenol, α-spinasterol, campestanol, $\Delta^7$-campestenol, 20α-hydroxycholesterol, brassicasterol, ergosterol, cerebrosterol, 7-dehydrocerebrosterol, cerebrostanol, $\Delta^7$-cerebrostenol, desmosterol, 7-dehydrodesmosterol, 3β-hydroxycholanic acid, and 3β-hydroxy-$\Delta^5$-cholenic acid.

Preferred examples of steroids of formula (1) include cholesterol, 7-dehydrocholesterol, cholestanol, coprostanol, $\Delta^7$-cholestenol, $\Delta^7$-coprostenol, β-sitosterol, 7-dehydro-β-sitosterol, stigmasterol, 7-dehydrostigmasterol, campesterol, and 7-dehydrocampesterol. Among these steroids, more preferred are cholesterol, 7-dehydrocholesterol, cholestanol, coprostanol, $\Delta^7$-cholestenol, and $\Delta^7$-coprostenol.

These steroids can be employed individually or in combination.

The steroid of formula (1) can be immobilized on the surface of the carrier by a method well known in the art. For example, the immobilization of the steroid on a carrier can be done by physically adsorbing the steroid on a surface of the carrier or by chemically binding a reactive derivative of the steroid to a surface of the carrier which surface has a functional group reactive with the derivative or is activated to be reactive with the derivative.

In the method of the present invention, it is preferred that the immobilized steroid be present in an amount of from 0.025 nmol/cm$^2$ to 250 nmol/cm$^2$, more preferably from 0.25 nmol/cm$^2$ to 25 nmol/cm$^2$ with respect to the surface area of the carrier.

With respect to the material, morphology, size and the like of the carrier to be used in the method of the present invention, there is no particular limitation as long as the method of the present invention can be satisfactorily performed. Examples of materials for carriers include polymers such as polystyrene, polyethylene, polypropylene, an acrylonitrile-butadiene-styrene copolymer, a butadiene-styrene copolymer, polycarbonate, polyvinyl chloride, polyvinylidene chloride, polyamide, polymethylmethacrylate, polymethylpentene, polyacetal, polyvinylacetate, polyvinylalcohol, polyvinyl butyral, polyisobutylene, a vinyl chloride-vinyl acetate copolymer, a fluororesin (polytetrafluoroethylene, a tetrafluoroethylene-ethylene copolymer, a perfluoroalkoxy copolymer, or the like), polyacrylonitrile, polystyrene acrylate, polyethylene terephthalate, polybutylene terephthalate, polyurethane, a urea resin, an epoxy resin, a melamine resin, a phenolic resin, an unsaturated polyester resin, a silicone resin, nitrocellulose, cellulose acetate, cellulose acetate butyrate, cellulose acetate propionate, cellulose propionate, ethylcellulose, carboxymethylcellulose, and polyvinylidene difluoride; and functional group-containing polymers obtained by, for example, a method in which in the production of the above-mentioned polymers, a compound having a functional group, such as carboxyl, nitrile, or primary or secondary amino, is introduced to the polymers by copolymerization, thereby introducing such a functional group to the polymers, or a method in which such a functional group is introduced at a surface of the above-mentioned polymers by a surface treatment. Further examples of materials for carriers include glass and metal.

In the present invention, the material, morphology, size and the like of the carrier can be the same as those of customarily known carriers which are usually used in the conventional immunological determination methods.

It is preferred that the carrier to be used in the present invention be a colloidal particle, a bead, a ball, a microtiter plate, a test tube, or a membrane. The diameter of a colloidal particle is generally from about 0.01 μm to about 10 μm. The diameter of a bead is generally not more than about 7 mm. The diameter of a ball is generally not more than about 10 mm.

An example of specific methods for immobilizing the steroid of formula (1) on a carrier by physical adsorption is explained below. For example, when a colloidal latex particle is used as a carrier, the steroid is contacted with colloidal latex particles in a hydrophilic or lipophilic solvent, most suitably ethanol or methanol, which can dissolve, disperse or suspend the steroid without adversely affecting the structure or the like of the colloidal latex particle. The steroid and the colloidal latex particles are then reacted with each other while stirring, shaking or allowing to stand still generally at 0° C. to 60° C., preferably 4° C. to 30° C., generally for 30 min. to 24 hours, preferably 1 hour to 10 hours. Thereafter, if desired, the resultant latex particles having the steroid immobilized thereon are washed with water or an appropriate buffer.

In the above-mentioned reaction, the concentration of the solids, i.e., the concentration of the latex particles in the reaction system is generally 0.01 (w/v) % to 10 (w/v) %, preferably 0.05 (w/v) % to 5 (w/v) %, and the concentration of the steroid in the reaction mixture is generally 0.1 µg/ml to 10 mg/ml, preferably 1 µg/ml to 1 mg/ml. The reaction system may contain water, or may contain any other solvent as long as the structure of the colloidal latex particle and the reaction are not adversely affected. Examples of such other solvents include chloroform, acetone, hexane, dichloroethane, propanol, isopropanol, xylene, toluene, benzene, ether, petroleum ether, methyl acetate, and ethyl acetate.

When a bead or a ball is used as a carrier, the immobilization of the steroid on a carrier can be conducted by a similar method to the above-described method for immobilizing the steroid on the colloidal latex particle, under reaction conditions which would not harm the structure of the bead or ball, while taking into consideration factors such as the surface area, volume and number of the bead or ball.

Further, when a microtiter plate is used as a carrier, the immobilization of the steroid on a carrier can be conducted, for example, by the following method. The steroid is dissolved, dispersed, or suspended in a hydrophilic or lipophilic solvent, most suitably ethanol or methanol, which can dissolve, disperse or suspend the steroid without adversely affecting the structure or the like of the microtiter plate, generally in a concentration of from 1 µg/ml to 10 mg/ml, preferably from 10 µg/ml to 1 mg/ml. Then, the obtained solution, dispersion or suspension is placed in the wells of the microtiter plate in an amount of generally from 25 µl to 200 µl per well, preferably from 50 µl to 100 µl per well, and allowed to stand still generally at 0° C. to 60° C., preferably at 4° C. to 30° C., generally for 30 min. to 24 hours, preferably 1 hour to 6 hours, thereby effecting a reaction. Thereafter, the wells are washed with water or an appropriate buffer.

In the above-mentioned reaction, the reaction system may contain water, or may contain any other solvent as long as the structure of the microtiter plate and the reaction are not adversely affected. Examples of such other solvents include chloroform, acetone, hexane, dichloroethane, propanol, isopropanol, xylene, toluene, benzene, ether, petroleum ether, methyl acetate, and ethyl acetate.

Another example of a method for immobilizing the steroid on a carrier is explained below. The steroid is dissolved, dispersed or suspended in a hydrophilic or lipophilic solvent, most suitably ethanol or methanol, which can dissolve, disperse or suspend the steroid without adversely affecting the structure and the like of the microtiter plate, in a concentration of from 100 ng/ml to 1 mg/ml, preferably from 1 µg/ml to 100 µg/ml. Then, the obtained solution, dispersion or suspension is placed in the wells of the microtiter plate in an amount of generally from 25 µl to 200 µl per well, preferably from 50 µl to 100 µl per well, and allowed to stand still at 20° C. to 90° C., preferably at 40° C. to 70° C., thereby evaporating and removing the solvent. Thereafter, the wells are washed with water or an appropriate buffer.

Further, for example, when a test tube is used as a carrier, the immobilization of the steroid on a carrier can be conducted by a similar method to the above-described method for immobilizing the steroid on the microtiter plate, under conditions which would not harm the structure of the test tube, while taking into consideration factors, such as the internal volume of the test tube.

Still further, for example, when a membrane is used as a carrier, the immobilization of the steroid on a carrier can be conducted, for example, by the following method. The steroid is dissolved, dispersed or suspended in a hydrophilic or lipophilic solvent, most suitably ethanol or methanol, which can dissolve, disperse or suspend the steroid without adversely affecting the structure of the membrane. The obtained solution, dispersion or suspension is contacted with the membrane by a customary method, for example, a method in which a dot-blotting is used, so that the steroid is immobilized on the membrane in an amount of generally from $0.025 \text{ nmol/cm}^2$ to $250 \text{ nmol/cm}^2$, preferably from $0.25 \text{ nmol/cm}^2$ to $25 \text{ nmol/cm}^2$ with respect to the surface area of the membrane.

In the above-mentioned immobilization method using a dot-blotting, the spot size is not particularly limited and can be selected in an appropriate range, and the solution, dispersion or suspension of the steroid may contain water, and may also contain any other solvent as long as the structure of the membrane and the reaction are not adversely affected. Examples of such other solvents include chloroform, acetone, hexane, dichloroethane, propanol, isopropanol, xylene, toluene, benzene, ether, petroleum ether, methyl acetate, and ethyl acetate.

Chemical binding of the steroid to a carrier can be conducted by a method in which a functional group, such as carboxyl, hydroxyl, thiol, primary amine, secondary amine, amido, nitro or aldehyde, is introduced to the steroid to thereby obtain a reactive derivative of the steroid and then, the obtained reactive derivative of the steroid is chemically bound to a surface of the carrier, wherein the surface of carrier has a functional group reactive with the functional group of the reactive derivative of the steroid or wherein the surface of carrier is activated to be reactive with the derivative, in accordance with a conventional method, for example, a method described in "Jikken-to-oyo: Affinity Chromatography (Experiments and Application: Affinity Chromatography)", Chibata, I., Tosa, T., Matsuo, Y.: pp.30–109, Kodansha K. K., Japan, Sep. 10, 1976, or a method described in "Koso Men-eki Sokuteiho (Enzyme Immunoassay)"; edited by Ishikawa, E., Kawai, T., Muroi, K., Third Edition, pp.75–151, Igaku Shoin K. K., Japan, May 15, 1987.

One example of a method for chemically binding the steroid to a carrier is explained below.

A steroid represented by formula (4):

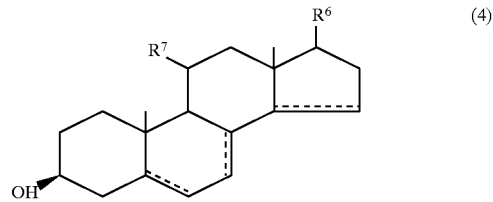

wherein $R^6$ is selected from the group consisting of a side chain moiety of cholesterol and a side chain moiety of cholic acid, wherein each of the side chain moieties is independently unsubstituted or substituted and saturated; $R^7$ is hydrogen or hydroxyl; and each dashed line represents a single bond or no bond, such that each dashed line and a solid line adjacent thereto together form a double bond or a single bond, provided that at least one dashed line represents a single bond,
is used as a starting material.

A functional group, such as carboxyl, primary amino, secondary amino, amido, nitro or aldehyde is introduced to the steroid of formula (4) by a method in which a 5,6-epoxy, 7,8-epoxy or 14,15-epoxy derivative of the steroid is prepared and then, a functional group is introduced and bonded to the 6th, 7th or 15th position of the steroid through a thioether linkage by a ring-opening reaction of the epoxy derivative of the steroid, in accordance with a method described by Hosoda, H., et al.; Chem. Phar. Bull., Vol. 28, pp.1294–1299, 1980. Subsequently, the resultant derivative of the steroid is bound to a surface of a carrier, wherein the surface of carrier has a functional group reactive with the derivative.

This method is more specifically explained below by way of example.

That is, for example, a steroid, represented by formula (4), having a double bond between the 7th and 8th positions, such as $\Delta^7$-cholestenol, $\Delta^7$-coprostenol, $\Delta^7$-stigmastenol, $\Delta^7$-campestenol or $\Delta^7$-cerebrostenol, is employed as a starting material and then, a carboxyl group is introduced at the 7th position of the starting material to thereby obtain a reactive derivative of the steroid.

Illustratively stated, the above-mentioned steroid as the starting material is contacted with a peroxide (preferably hydrogen peroxide) and an alkali reagent (preferably sodium hydroxide or potassium hydroxide) in a hydrophilic organic solvent (preferably methanol or ethanol) which can dissolve, disperse or suspend the steroid, and the resultant mixture is subjected to a reaction while stirring, shaking or allowing to stand still generally at 0° C. to 40° C., preferably 0° C. to 10° C., generally for 30 min. to 12 hours, preferably 1 hour to 6 hours to thereby obtain a reaction mixture containing an epoxy derivative of the starting material. Subsequently, the reaction mixture is neutralized.

The above-mentioned reaction is conducted under conditions such that the concentration of the steroid as the starting material is generally from 0.01 mmol/ml to 1 mmol/ml, preferably from 0.05 mmol/ml to 0.5 mmol/ml, the concentration of the peroxide is generally from 0.1 (w/v) % to 10 (w/v) %, preferably from 0.5 (w/v) % to 5 (w/v) %, the concentration of the alkali reagent is generally from 0.5 (w/v) % to 10 (w/v) %, preferably from 1 (w/v) % to 5 (w/v) %, and the water content is preferably not more than 20 (v/v) %.

The isolation of the produced epoxy derivative can be conducted in accordance with a conventional method described, for example, in "Sei-kagaku Kenkyu-ho I (Methods for Biochemical Research I)", Seventh Edition; edited by Ando E., Terayama, H., Nishizawa, K., and Yamakawa, T. and published by Asakura Shoten K. K., Japan, pp.49–96 (Mar. 20, 1973).

Subsequently, the obtained epoxy derivative is contacted with mercaptomonocarboxylic acid (preferably 2-mercaptoacetic acid, 3-mercaptopropionic acid or the like) and an alkali reagent (preferably sodium hydroxide or potassium hydroxide) in a hydrophilic organic solvent, most suitably methanol or ethanol, which can dissolve, disperse or suspend the epoxy derivative, and the resultant mixture is subjected to a reaction while stirring, shaking or allowing to stand still, generally at 0° C. to 60° C., preferably 10° C. to 40° C., generally for 30 min. to 12 hours, preferably 1 hour to 6 hours, followed by changing the pH value of the reaction mixture to a value in the acidic range, thereby obtaining a derivative of the steroid (which is to be used as a starting material) which has carboxyl bonded thereto at the 7th position through a thioether linkage.

The above-mentioned reaction is conducted under conditions such that, in the reaction system, the concentration of the epoxy derivative is generally from 0.01 mmol/ml to 1 mmol/ml, preferably from 0.05 mmol/ml to 0.5 mmol/ml, the concentration of the mercaptomonocarboxylic acid is generally from 0.05 mmol/ml to 5 mmol/ml, preferably from 0.1 mmol/ml to 1 mmol/ml, the concentration of the alkali reagent is generally from 0.5 (w/v) % to 10 (w/v) %, preferably from 1 (w/v) % to 5 (w/v) %, and the water content is preferably not more than 20 (v/v) %.

The reaction system may contain dioxane and the like. The isolation of the produced functional group-containing derivative may be done in accordance with the same method as that for the isolation of the epoxy derivative.

In the above method, among steroids represented by formula (4), a steroid having a double bond between the 7th and 8th positions, such as $\Delta^7$-cholestenol, $\Delta^7$-coprostenol, $\Delta^7$-stigmastenol, $\Delta^7$-campestenol or $\Delta^7$-cerebrostenol, is employed as a starting material and then, carboxyl is introduced at the 7th position of the starting material, to thereby obtain a reactive derivative of the steroid, such as a cholestenol derivative, coprostenol derivative, stigmastenol derivative, campestenol derivative or cerebrostenol derivative which has carboxyl bonded at the 7th position through a thioether linkage.

Further, in accordance with the above method, it is possible that a steroid, represented by formula (4), having a double bond between the 5th and 6th positions, such as cholesterol, β-sitosterol, campesterol or cerebrosterol, is employed as a starting material and then, carboxyl is introduced at the 6th position of the starting material, to thereby obtain a reactive derivative of the steroid, such as a cholestanol derivative, stigmastanol derivative, campestanol derivative or cerebrostanol derivative which has carboxyl bonded at the 6th position through a thioether linkage.

The carboxyl-introduced, reactive derivative of the steroid can be reacted with and linked to amino present on a surface of a carrier by a known method, such as the acid anhydride method, the carbodiimide method or the N-hydroxysuccinimide method, to thereby immobilize the steroid on the surface of carrier.

The immobilization of streptolysin O on the surface of carrier having immobilized thereon the steroid can be conducted, for example, by reacting the carrier having the steroid immobilized thereon with streptolysin O in water or an appropriate buffer.

In the present invention, it is preferred that the immobilized streptolysin O of the streptolysin O-immobilized carrier be present in an amount of from 0.001 pmol/cm$^2$ to 1 nmol/cm$^2$, more preferably from 0.01 pmol/cm$^2$ to 100 pmol/cm$^2$ with respect to the surface area of the carrier.

The streptolysin O to be used in the present invention can be of any type, as long as it exhibits a binding activity to the steroid used in the present invention and is susceptive to antigen-antibody reaction with antistreptolysin O antibody. Streptolysin O, a derivative thereof and a variant thereof can be used. These materials may be those which are produced, for example, from group A, B or C hemolytic *streptococci*, or which are produced, by genetic recombinant techniques, from host cells, e.g., transformed microorganisms, such as *Escherichia coli*, yeast, and the like.

In the present invention, any streptolysin O-like substance which exhibits a binding activity to the steroid used in the present invention and is susceptive to antigen-antibody reaction with antistreptolysin O antibody, can be used instead of streptolysin O. For example, a synthesized protein or synthesized peptide, which has an amino acid structure such that streptolysin O lacks a part or whole of a hemolytically active site thereof, may be used. Streptolysin O used in the present invention need not necessarily be of high purity.

However, when streptolysin O contains an inhibitory substance which would inhibit a binding reaction of the streptolysin O to a steroid of formula (1) or to antistreptolysin O antibody, it is desirable to appropriately purify the streptolysin O to remove the inhibitory substance.

It is convenient to use commercially available streptolysin O. Examples of commercially available streptolysin O products include those which are respectively sold by Eiken Chemical Co., Ltd., Japan; Nissui Pharmaceutical Co., Ltd., Japan; Corporation Japan Lyophilization Laboratory, Japan; Difco Laboratories, U.S.A.; and Sigma Chemical Company, U.S.A.

With respect to buffers to be used in the present invention, there is no particular limitation, and buffers which are customarily used can be employed. It is desirable to use buffers having a pH value in the range of from 5 to 9, preferably from 6 and 8. For example, phosphate buffer, boric acid buffer, carbonic acid buffer, tris buffer, Veronal buffer, and Good's buffers (for example, HEPES buffer, PIPES buffer, and MES buffer) can be used.

If desired for stabilization of streptolysin O or prevention of non-specific adsorption of proteins on the carrier, additives such as bovine serum albumin (BSA), gelatin, skim milk, protein (e.g., milk-derived protein), saccharide, glycerol, ethylene glycol, a chelating agent, and a reducing agent, may be added to water or a buffer to be used. These additives can be used in amounts which are used in the conventional immunological determination methods for antistreptolysin O antibody which methods utilize antigen-antibody reaction. Streptolysin O is relatively unstable in an aqueous solution and, therefore, for the stabilization thereof, it is desirable to add, to water or a buffer which are to be used, an additive, such as bovine serum albumin (BSA), gelatin, skim milk or protein (e.g., milk-derived protein) in a concentration of generally from 0.01 (w/v) % to 10 (w/v) %, preferably from 0.1 (w/v) % to 1 (w/v) %.

If desired for preventing non-specific adsorption of proteins on the carrier, a carrier having immobilized thereon the steroid may be treated with a treating solution obtained by dissolving an additive, such as bovine serum albumin (BSA), gelatin, skim milk, or protein (such as milk-derived protein) in water or a buffer. The concentration of the additive in the treating solution can be appropriately selected from the concentration ranges of such a treating solution usually used, for example, in the conventional immunological determination methods utilizing antigen-antibody reaction. For example, the concentration of the additive in the treating solution is generally from 0.05 (w/v) % to 10 (w/v) %, preferably 0.5 (w/v) % to 5 (w/v) %.

In the present invention, the conditions for practicing the method for immobilizing streptolysin O on a carrier having immobilized thereon the steroid may be varied depending on factors such as the purity of streptolysin O, the streptolysin O concentration of a streptolysin O-containing solution to be used, the type of the carrier, and the principle of a respective assay method used for determining antistreptolysin O antibody bound to the binding agent. For example, taking into consideration the above factors, the immobilization of streptolysin O on a carrier having the steroid immobilized thereon can be conducted in accordance with the procedure described below.

When it is desired that streptolysin O be immobilized on colloidal latex particles having the steroid immobilized thereon, the immobilization of streptolysin O can be conducted, for example, by the following method.

An aqueous solution having a protein content of 0.5 mg/ml to 1 mg/ml, wherein the protein has a streptolysin O content of 5% to 10% by weight, is provided, and the streptolysin O solution is diluted with water or the above-mentioned buffer 1- to 10,000-fold, preferably 10- to 1,000-fold. In the resultant diluted streptolysin O solution are suspended latex particles having the steroid immobilized thereon in such an amount that the concentration of the latex particles (i.e., the solids concentration) is generally 0.01 (w/v) % to 10 (w/v) %, preferably 0.05 (w/v) % to 5 (w/v) %. The resultant suspension is subjected to a reaction while allowing to stand still, stirring or shaking generally at 0° C. to 40° C., preferably 4° C. to 30° C., generally for 10 min. to 24 hours, preferably 30 min. to 12 hours. Thereafter, if desired, the resultant streptolysin O-immobilized latex particles may be washed with water or a buffer.

The streptolysin O-immobilized latex particles obtained by the above-mentioned method can be advantageously used for determining antistreptolysin O antibody, based on the principle of, for example, immune agglutination assays.

When a steroid-immobilized bead or a steroid-immobilized ball is used as a carrier, the immobilization of streptolysin O on a steroid-immobilized carrier can be conducted by a similar method to the above-described method for immobilizing streptolysin O on the steroid-immobilized colloidal latex particles, while taking into consideration factors such as the surface area, volume and number of the bead or ball.

The streptolysin O-immobilized bead or ball obtained by the above-mentioned method can be advantageously used for determining antistreptolysin O antibody, for example, by the enzyme immunoassay, radioimmunoassay, or fluoroimmunoassay.

When it is desired that streptolysin O be immobilized on a microtiter plate having the steroid immobilized thereon, the immobilization of streptolysin O can be conducted, for example, by the following method.

An aqueous solution having a protein content of 0.5 mg/ml to 1 mg/ml, wherein the protein has a streptolysin O content of 5% to 10% by weight, is provided, and the streptolysin O solution is diluted, with water or the above-mentioned buffer, generally 10- to 10,000-fold, preferably 100- to 1,000-fold. The diluted solution is placed in the wells of the steroid-immobilized microtiter plate in an amount of generally from 25 µl to 200 µl per well, preferably from 50 µl to 100 µl per well, and allowed to stand still generally at 0° C. to 40° C., preferably at 4° C. to 30° C., generally for 10 min. to 24 hours, preferably 30 min. to 10 hours (thereby effecting a reaction). Thereafter, the wells are washed with water or an appropriate buffer.

The streptolysin O-immobilized microtiter plate obtained by the above-mentioned method can be advantageously used for determining antistreptolysin O antibody, for example, by the enzyme immunoassay, radioimmunoassay, or fluoroimmunoassay.

Further, for example, when a steroid-immobilized test tube is used as a carrier, the immobilization of streptolysin O on a steroid-immobilized carrier can be conducted by a similar method to the above-described method for immobilizing the streptolysin O on the steroid-immobilized microtiter plate, while taking into consideration factors such as the internal volume of the test tube.

The streptolysin O-immobilized test tube obtained by the above-mentioned method can be advantageously used for determining antistreptolysin O antibody, for example, by the enzyme immunoassay, radioimmunoassay, or fluoroimmunoassay.

Further, when it is desired that streptolysin O be immobilized on a membrane having the steroid immobilized thereon, the immobilization of streptolysin O can be conducted, for example, by the following method.

An aqueous solution having a protein content of 0.5 mg/ml to 1 mg/ml, wherein the protein has a streptolysin O content of 5% to 10% by weight, is provided, and the streptolysin O solution is diluted, with water or the above-mentioned buffer, generally 10- to 10,000-fold, preferably 100- to 1,000-fold. The diluted solution is contacted with the steroid-immobilized membrane, for example, in an appropriate reaction vessel, or is contacted with the steroid-immobilized membrane by dripping the solution on portions of the membrane. Then, the membrane is allowed to stand still or shaken generally at 0° C. to 40° C., preferably 4° C. to 30° C., generally for 5 min. to 24 hours, preferably 10 min. to 10 hours. Thereafter, the resultant streptolysin O-immobilized membrane is washed with water or the above-mentioned buffer.

The streptolysin O-immobilized membrane obtained by the above-mentioned method can be advantageously used for determining antistreptolysin O antibody, for example, by immunostaining method.

In the method of the present invention for immunologically determining antistreptolysin O antibody, a test sample solution containing antistreptolysin O antibody is contacted with and reacted with a specific binding agent (i.e., the above-described specific streptolysin O-immobilized carrier), under conditions suitable for the formation of an antigen-antibody complex, thereby selectively binding the antistreptolysin O antibody to the binding agent by antigen-antibody reaction, and, then, an amount of the antistreptolysin O antibody bound to the binding agent is determined.

Examples of test sample solutions to be used in the method of the present invention include body fluids such as serum, plasma, saliva and urine, a tissue extract, and a supernatant of tissue culture. These test sample solutions may be used as they are or may be used after being appropriately diluted with water or the above-mentioned buffer, taking into consideration factors such as the principle for the determination of the anti-streptolysin O antibody bound to the binding agent, the sensitivity of detection, and the range of measurement.

With respect to the reaction conditions under which the method of the present invention for immunologically determining antistreptolysin O antibody is practiced, there is no particular limitation as long as the antigen-antibody reaction is not inhibited and the properties of the reagents to be used are not impaired (for example, when a labeled substance is used, the detectable properties of the labeled substance should not be impaired). Taking into consideration factors such as the principle for determining the antistreptolysin O antibody bound to the binding agent, suitable reaction conditions can be appropriately selected from those reaction conditions generally used in the conventional determination methods.

In the present invention, for example, when streptolysin O-immobilized colloidal latex particles are used as the binding agent, the method of the present invention can be advantageously applied, for example, to the latex agglutination tests such as the latex slide agglutination method [see Satomi Shibata et al., "Kiki•Shiyaku (Equipment and Reagents)", Vol. 11, pp. 338–342, 1988]. Specifically, in this case, streptolysin O-immobilized latex particles and a test sample solution are mixed with each other on an evaluation plate, and occurrence or non-occurrence of agglutination of the latex particles by the antigen-antibody reaction is visually examined.

Also, when streptolysin O-immobilized colloidal latex particles are used as the binding agent, the method of the present invention can be advantageously applied to the latex photometric immunoassay (LPIA) [see Ikunosuke Sakurabayashi et al., "Nippon Rinsho (Japanese Journal of Clinical Medicine)", Vol. 48, Supplementary Edition (Vol. II), pp. 1356–1361, 1990]. In this case, the streptolysin O-immobilized latex particles and a test sample solution are mixed with each other, and a turbidity produced by the antigen-antibody reaction is optically measured. The antistreptolysin O antibody is determined by referring to a calibration curve obtained with respect to a standard solution containing antistreptolysin O antibody.

In addition, when streptolysin O-immobilized colloidal latex particles are used as the binding agent, the method of the present invention can be advantageously applied to the nephelometric immunoassay (NIA) [see Yasuko Yamagishi, "Rinsho-kensa (Laboratory Examinations)", Vol. 23, Supplementary Edition, pp. 1286–1289, 1979]. In this case, the streptolysin O-immobilized latex particles and a test sample solution are mixed with each other, an aggregate produced by antigen-antibody reaction is irradiated with light (laser beam), and the intensity of the scattered beam is measured, whereafter antistreptolysin O antibody is determined by referring to a calibration curve obtained with respect to a standard solution containing antistreptolysin O antibody.

Further, when streptolysin O-immobilized colloidal latex particles are used as the binding agent, the method of the present invention can be advantageously applied to the counting immunoassay [see Kouichi Hashimoto et al., "Kensa-to-gijutsu (Examinations and Techniques)", Vol. 22, No. 5, pp. 67–68, Supplementary Edition, 1994]. In this case, the streptolysin O-immobilized latex particles and a test sample solution are mixed with each other and then, an aggregate produced by antigen-antibody reaction is measured with respect to the size and number. The antistreptolysin O antibody is determined by referring to a calibration curve obtained with respect to a standard solution containing antistreptolysin O antibody.

On the other hand, when a streptolysin O-immobilized microtiter plate, a streptolysin O-immobilized bead, a streptolysin O-immobilized ball or a streptolysin O-immobilized test tube is used as the binding agent, the method of the present invention can be advantageously applied, for example, to the enzyme immunoassay. In this case, the streptolysin O-immobilized carrier and a test sample solution are reacted with each other to form an antigen-antibody complex and then, antibody (against antistreptolysin O antibody) labeled with a labeling agent is reacted with the complex, whereupon the activity of the labeling agent bound to the carrier through the complex is measured. The antistreptolysin O antibody is determined by referring to a calibration curve obtained with respect to a standard solution containing antistreptolysin O antibody.

Further, by utilizing the property of biotin (which is one type of vitamin B) that it specifically binds to avidin, which is a basic glycoprotein present in the albumen, the above-mentioned determination method by enzyme immunoassay can be modified as follows. Antibody (against antistreptolysin O antibody) having biotin bound thereto is used instead of the labeled antibody, and avidin or streptoavidin labeled with a labeling agent is reacted with the biotin bound to the antibody, whereafter the activity of the labeling agent bound to the carrier through the antigen-antibody complex is measured. The antistreptolysin O antibody is determined by referring to a calibration curve obtained with respect to a standard solution containing antistreptolysin O antibody.

With respect to the types of the labeled antibody and the biotin-bound antibody for use in the determination method using the enzyme immunoassay, there is no limitation as long as they can bind to antistreptolysin O antibody contained in the test sample solution. Any of polyclonal antibody, monoclonal antibody, and enzymolytic fragments thereof [e.g. F(ab')$_2$, F(ab)$_2$, Fab' and Fab] can be used. The antibody may be one which has been derived from any animal species, and may be one which has been produced by genetic recombinant techniques from host cells, e.g., transformed microorganisms, such as *Escherichia coli,* yeast, and the like.

With respect to the labeling agent, it can be appropriately selected from those generally used in the enzyme immunoassay. Preferred examples of labeling agents include peroxidase, alkaline phosphatase, β-galactosidase, and glucose oxidase.

The detection of the activity of enzymes can be conducted in accordance with the procedure described, for example, in "Kouso Men-eki Sokutei-ho (Enzyme Immunoassay)", "Tanpakushitsu-Kakusan-Kouso (Protein/Nucleic Acid/Enzyme)" Supplement, No.31; edited by Tsunehiro Kitagawa, Toshio Nambara, Akio Tsuji, and Eiji Ishikawa; and published by Kyoritsu Shuppan K. K., Japan, pp.51–63 (Sep. 10, 1987).

Further, when a streptolysin O-immobilized microtiter plate, a streptolysin O-immobilized bead, a streptolysin O-immobilized ball or a streptolysin O-immobilized test tube is used as the binding agent, the method of the present invention can be advantageously applied to the enzyme immunoassay, based on the principle of the competitive binding assay, which is one of the antibody determination methods described in "Koso Men-eki Sokuteiho (Enzyme Immunoassay)"; edited by Ishikawa, E., Kawai, T., and Muroi, K., Third Edition, published by Igaku Shoin K. K., Japan, pp.31–54 (May 15, 1987).

In the above-mentioned enzyme immunoassay based on the principle of the competitive binding assay, enzyme-labeled antistreptolysin O antibody is employed. The enzyme-labeled antistreptolysin O antibody can be obtained by labeling antibody derived from the serum of a patient infected with group A hemolytic streptococci, or labeling antibody derived from the antiserum obtained by immunizing an aminal with an immunogen comprised of streptolysin O, in accordance with the methods described in "Kouso-Men-eki Sokutei-ho (Enzyme Immunoassay)", "Tanpakushitsu-Kakusan-Kouso (Protein/Nucleic Acid/Enzyme)" Supplement, No.31; edited by Tsunehiro Kitagawa, Toshio Nambara, Akio Tsuji, and Eiji Ishikawa, and published by Kyoritsu Shuppan K. K., Japan, pp.37–45 (Sep. 10, 1987). The enzyme-labeled antistreptolysin O antibody can also be obtained by labeling monoclonal antibody prepared against streptolysin O in accordance with the methods described in "Men-eki-kenkyu-ho Handbook (Handbook for Immunological Research)"; edited by Hiromi Fujiwara and Junji Yodoi, and published by Chugai-Iyaku-Sha K. K., Japan, pp.61–75 (Sep. 20, 1992). The determination of the labeled enzyme and the detection of the activity of enzyme can be conducted in accordance with the above-mentioned methods.

In addition to the above-mentioned enzyme immunoassay, any other conventional method, for example, the radioimmunoassay, the fluoroimmunoassay and the like may also be employed. In the radioimmunoassay and the fluoroimmunoassay, a radioactive substance and a fluorescent substance are used, respectively, instead of the enzyme as a labeling agent in the enzyme immunoassay.

Further, when a streptolysin O-immobilized membrane is used as the binding agent, the method of the present invention can be advantageously applied, for example, to the immunostaining method. In this case, the streptolysin O-immobilized membrane and a test sample solution are reacted with each other to form an antigen-antibody complex and then, antibody (against antistreptolysin O antibody) labeled with a labeling agent is reacted with the complex, whereupon the activity of the labeling agent bound to the carrier through the complex is visually examined or measured by a densitometer.

The method for confirming or determining a product of the antigen-antibody reaction is not particularly limited. Not only manual methods, but also automated methods using an automated analyzer are employable. For example, when the method of the present invention is applied to the latex photometric immunoassay (LPIA), automated analyzers, such as Hitachi 705, 7050, 7150, 736, and 7070 (manufactured and sold by Hitachi, Ltd., Japan) can be used. These automated analyzers automatically perform operations such as dispensation of a test sample solution, dispensation of a reagent, washing, measurement of absorbance, and data processing. Specifically, for example, these automated analyzers perform the following operations. Streptolysin O-immobilized latex particles and a test sample solution are mixed with each other in a reaction cell. After a predetermined period of time, absorbance is measured at an appropriate wavelength selected from conventional measurement conditions, preferably at a wavelength of 400 nm to 950 nm, while conducting a blank correction. Then, the results of the measurement of the absorbance are compared with a calibration curve obtained with respect to a standard solution containing antistreptolysin O antibody, thereby determining the antistreptolysin O antibody in the test sample solution.

Further, for example, when the method of the present invention is applied to the enzyme immunoassay, using as the binding agent a streptolysin O-immobilized microtiter plate or a streptolysin O-immobilized test tube, an automated assay system, such as BECKMAN Biomek 1000 Automated Laboratory Workstation (manufactured and sold by Beckman Instruments, Inc., U.S.A.) or CELL ASSAY-2000 ROBOTIC ASSAY SYSTEM (manufactured and sold by Moritex Corporation, Japan) can be used. These automated assay systems automatically perform operations such as dispensation of a test sample solution, dispensation of a reagent, washing, measurement of absorbance, and data processing. Specifically, these automated assay systems perform, for example, the following operations. A streptolysin O-immobilized microtiter plate or a streptolysin O-immobilized test tube is successively reacted with a test sample solution, enzyme-labeled antibody and a substrate solution, wherein a washing operation is inserted between the above respective reactions. If desired, an enzyme inhibitor solution is added to the resultant reaction mixture to terminate the reaction. Then, the coloration produced by the enzyme reaction between the labeling enzyme and the substrate used is measured at an appropriate wavelength selected from conventional measurement conditions. The results of the measurement of the coloration are compared with a calibration curve obtained with respect to a standard solution containing antistreptolysin O antibody, thereby determining the antistreptolysin O antibody in the test sample solution.

When the method of the present invention is applied, for example, to the enzyme immunoassay, using as the binding agent a streptolysin O-immobilized bead, an automated assay system, such as Aloka AEC-2000 POSEIDON II (manufactured and sold by Aloka Co., Ltd., Japan) can be used. This automated assay system automatically performs operations such as dispensation of a test sample solution, dispensation of a reagent, washing, measurement of absorbance, and data processing. Specifically, this automated assay system performs, for example, the following operations. A streptolysin O-immobilized bead is successively reacted with a test sample solution, enzyme-labeled antibody and a substrate solution, wherein a washing operation is inserted between the above respective reactions. If desired, an enzyme inhibitor solution is added to the resultant reaction mixture to terminate the reaction. Then, the coloration produced by the enzyme reaction between the labeling enzyme and the substrate used is measured at an appropriate wavelength selected from conventional measurement conditions. The results of the measurement of the coloration are compared with a calibration curve obtained with respect to a standard solution containing antistreptolysin O antibody, thereby determining the antistreptolysin O antibody in the test sample solution.

From the viewpoint of convenience, it is preferred that some or all of the reagents necessary for practicing the method of the present invention be provided in the form of a reagent kit. Such a reagent kit is also advantageous when an automated analyzer is used in practicing the method of the present invention.

An example of such a reagent kit is a kit comprising (A) a carrier having immobilized thereon the steroid to be used in the present invention, and (B) a streptolysin O-containing solution. It is especially preferred that, in addition to or instead of the above-mentioned reagents (A) and (B), the reagent kit comprise (C) a streptolysin O-immobilized carrier as the binding agent, which has been prepared by reacting the above-mentioned reagents (A) and (B) with each other. The reagent kit in the present invention may also contain other appropriate reagents, for example, a buffer, a standard substance, labeled antibody, a substrate, a solvent for a substrate, and a reaction terminator.

EXAMPLES

Hereinbelow, the present invention will be illustrated with reference to the following Examples and FIGS. 1 through 6, which however should not be construed as limiting the scope of the present invention.

Figure 3:
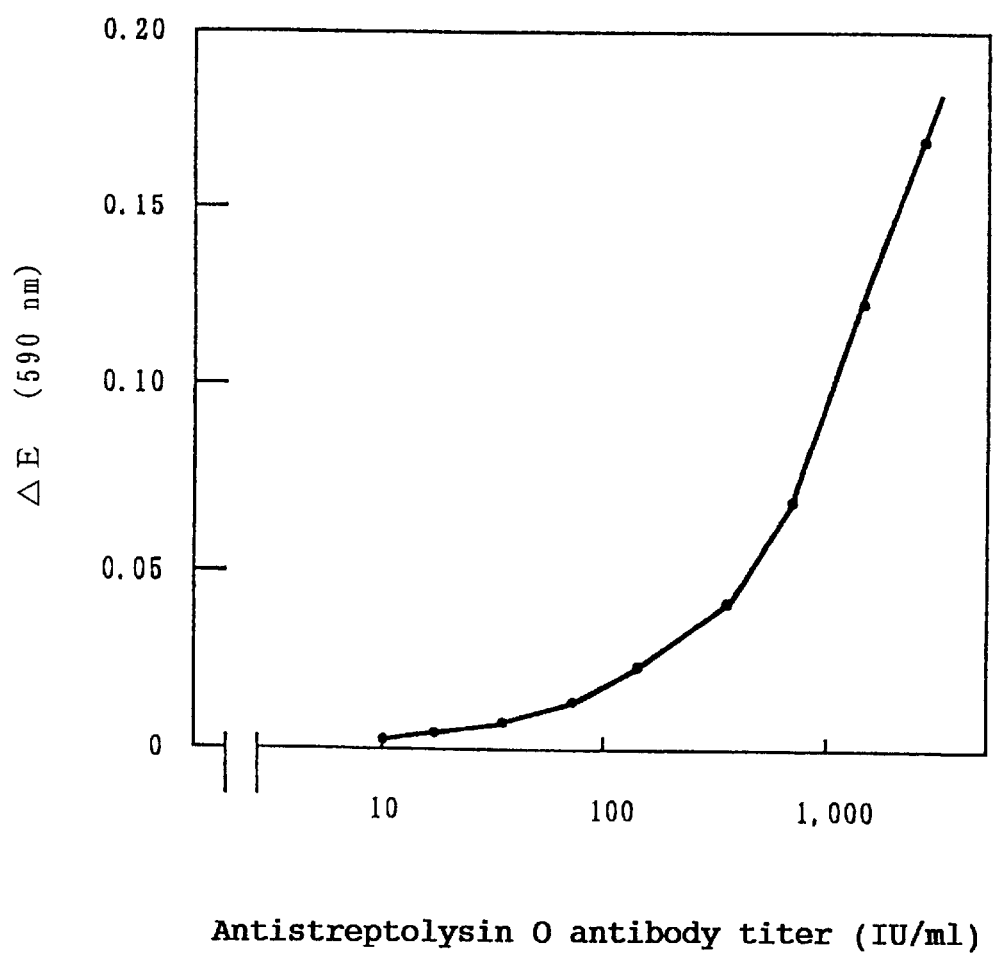
FIG. 3 is a graph showing a calibration curve used in Example 3, illustrating the relationship between the antistreptolysin O antibody titer and the absorbance at 590 nm, wherein the calibration curve has been obtained by the method of the present invention, using a standard solution containing antistreptolysin O antibody as a test sample solution and using streptolysin O-immobilized latex particles as a binding agent.
Figure 4:
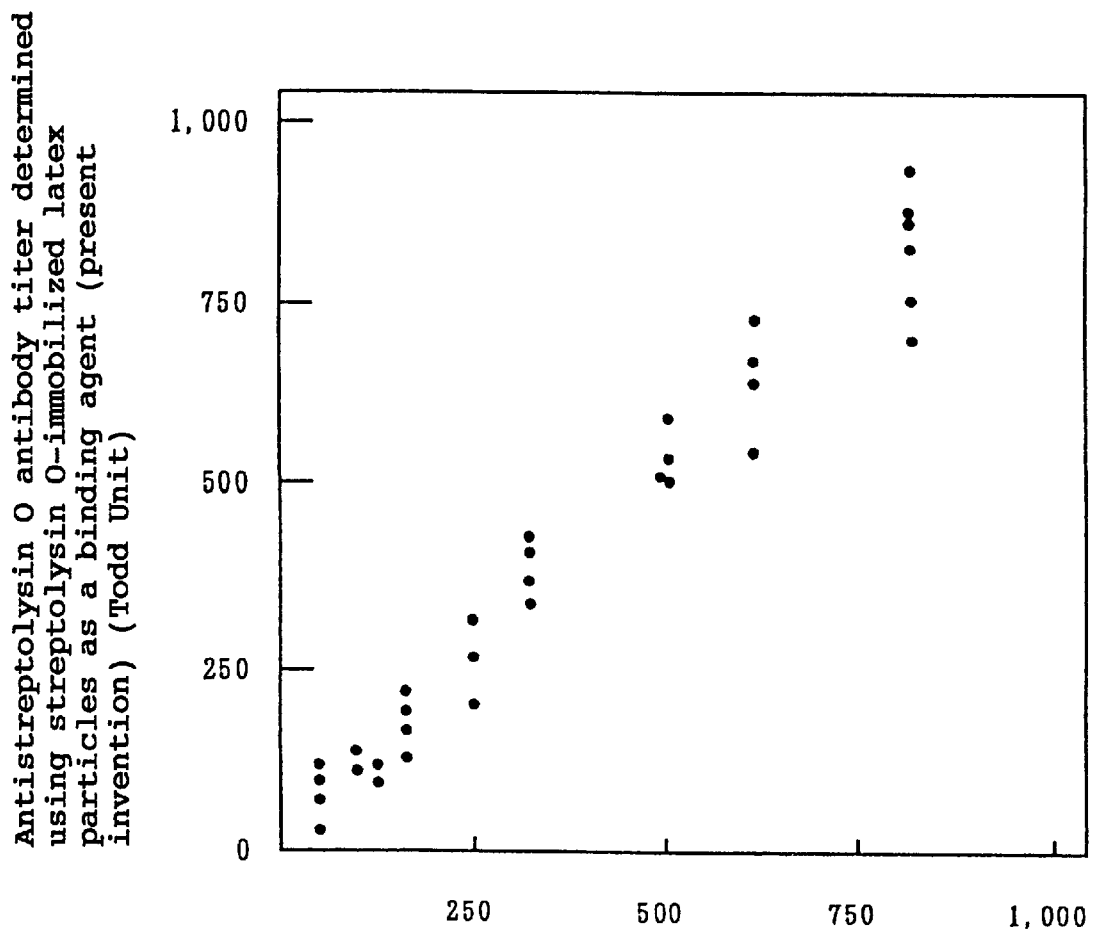
FIG. 4 is a graph showing the relationship between the antistreptolysin O antibody titer determined in Example 3 by the method of the present invention using streptolysin O-immobilized latex particles as a binding agent, and the antistreptolysin O antibody titer determined by the Rantz-Randall method.
Figure 5:
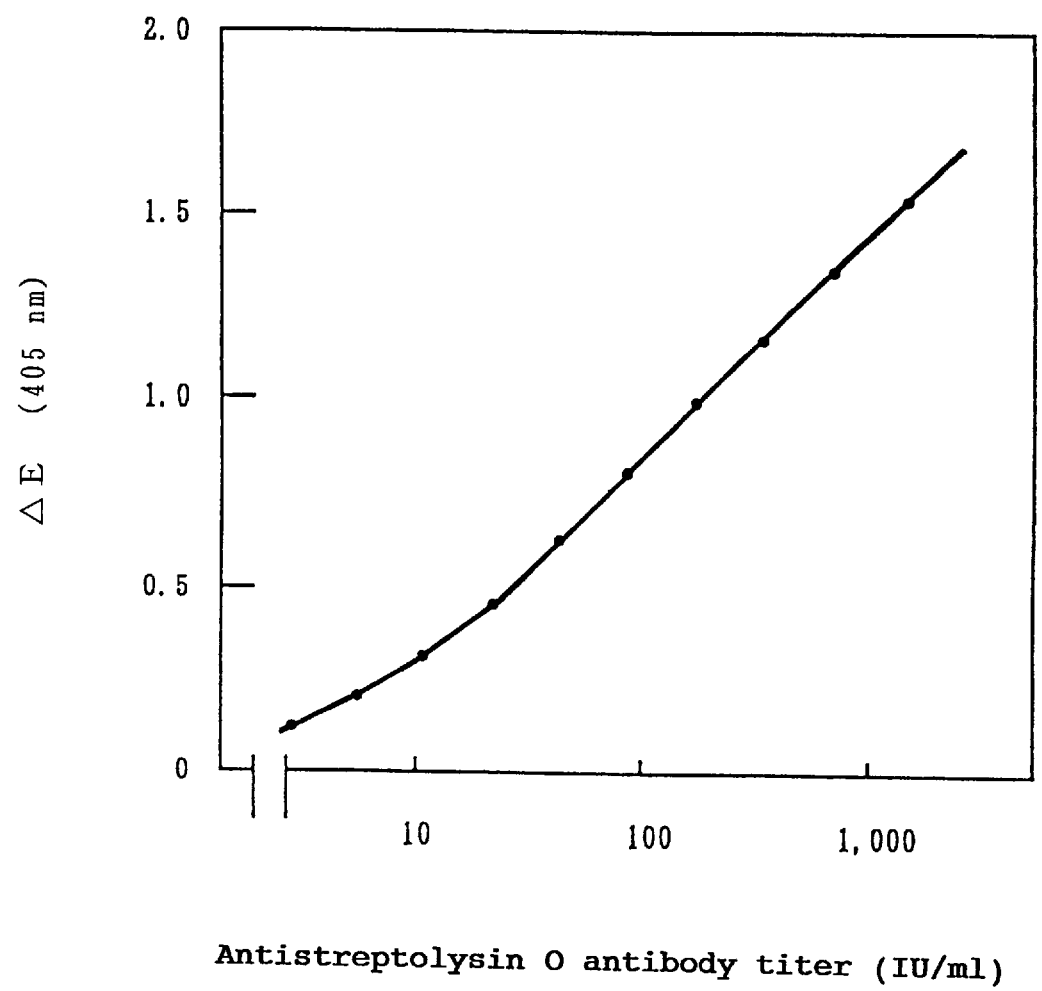
FIG. 5 is a graph showing a calibration curve used in Example 4, illustrating the relationship between the antistreptolysin O antibody titer and the absorbance at 405 nm, wherein the calibration curve has been obtained by the method of the present invention, using a standard solution containing antistreptolysin O antibody as a test sample solution and using a streptolysin O-immobilized microtiter plate as a binding agent.
Figure 6:
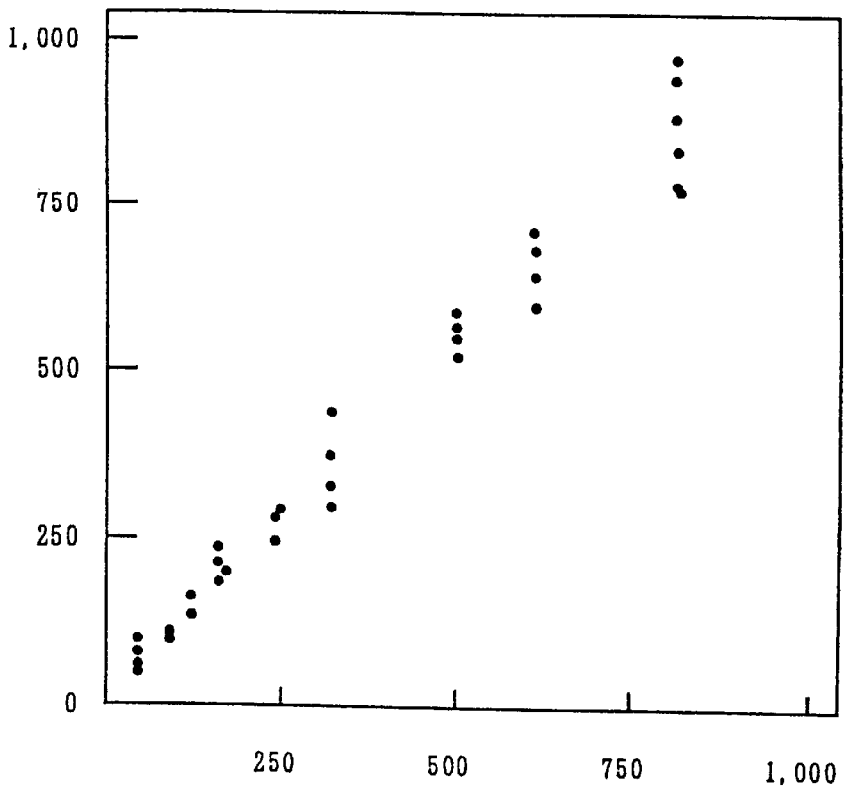
FIG. 6 is a graph showing the relationship between the antistreptolysin O antibody titer determined in Example 4 by the method of the present invention using a streptolysin O-immobilized microtiter plate as a binding agent, and the antistreptolysin O antibody titer determined by the Rantz-Randall method.

In FIGS. 3 and 5, the term "IU" (i.e., international unit) is indicated. In FIGS. 4 and 6, the term "Todd Unit" is indicated. The international unit is a unit defined by WHO. Todd unit means an amount of antistreptolysin O antibody which can neutralize streptolysin O of an amount 2.5 times a minimal amount (minimal hemolytic dose) of streptolysin O at which 0.5 ml of a 5 (v/v) % rabbit erythrocyte can be completely lysed. The international unit is substantially equivalent to Todd unit.

Example 1

Examination of reactivity of an immobilized steroid with streptolysin O
(1) Preparation of Streptolysin O Group A hemolytic streptococci (*Streptococcus pyogenes*) type 3 strain D58X (ATCC 12383) was inoculated in 2 liters of Todd-Hewitt Broth (Difco Laboratories, U.S.A.) and incubated at 37° C. for 12 hours, followed by centrifugation and filtration to recover a sterile filtrate. Then, saturated ammonium sulfate was added to the filtrate to a concentration of 40% saturation, to form a precipitate. The precipitate was separated, and dissolved in 100 ml of purified water to obtain a solution.

The obtained solution was dialyzed against purified water and PBS to remove the ammonium sulfate. With respect to the resultant solution, gel filtration was conducted using Sephadex G-100 which had been equilibrated with PBS (containing 1 liter of gel), and a streptolysin O fraction was recovered utilizing hemolytic activity as a criterion. The fraction was condensed to obtain 11 ml of a sample solution, which contained streptolysin O exhibiting an absorbance of 0.800 at 280 nm and a hemolytic activity of 8,192 hemolytic units (HU)/ml.

The assay of hemolytic activity was conducted by the following method. Fresh defibrinated erythrocytes obtained from a rabbit (which are available from Nippon Bio-Test Laboratories K.K., Japan) were washed with PBS five times by centrifugation, and PBS was added thereto to prepare a 1 v/v % erythrocyte suspension.

With respect to the above-obtained sample solution containing streptolysin O, serial two-fold dilutions with PBS were conducted. 1 ml of each serial dilution was individually mixed with 2 ml of the above-prepared 1 v/v % erythrocyte suspension in a glass tube, followed by incubation at 37° C. for 30 minutes. Subsequently, with respect to each tube, measurement of hemolysis was done to determine the maximum fold number of dilutions at which 100% hemolysis was exhibited. The number obtained was defined as a HU value per 1 ml of the sample solution containing streptolysin O.
(2) Production of a Cholesterol-Immobilized Carrier 100 μl of an ethanol solution, containing cholesterol (available from Nakarai Chemical Ltd., Japan) in a concentration of 1 mg/ml, was placed in each well of a microtiter plate (available from Sumitomo Bakelite Co., Ltd., Japan) and then, the plate was allowed to stand at 60° C. for 2 hours to evaporate and remove the solvent, to thereby prepare a cholesterol-immobilized microtiter plate. The same procedure as above was repeated, except that ethanol containing no cholesterol was used instead of the ethanol solution containing cholesterol, thereby obtaining a microtiter plate having no cholesterol immobilized thereon, which was for use as a control.
(3) Reaction of a Cholesterol-Immobilized Carrier with a Solution Containing Streptolysin O The sample solution containing streptolysin O prepared in item (1) above was diluted 20-fold with PBS, and 50 μl of the resultant dilution was placed in each well of each of two types of microtiter plates produced in item (2) above, having cholesterol immobilized thereon and having no cholesterol immobilized thereon, respectively. Then, with respect to each microtiter plate, a reaction was allowed to proceed at room temperature for 2 hours. The resultant reaction mixture was recovered from each well, and subjected to testings [i.e., SDS-polyacrylelectrophoresis (SDS-PAGE) and hemolytic activity assay described in item (1) above]. The results of the testings of each reaction mixture were compared with those obtained with respect to the original sample solution before the reaction.

The above SDS-PAGE was conducted, using a 12.5 w/v % polyacrylamide gel, substantially in accordance with the method of Laemmli, U.K. (Nature, 227; pp680–685, 1970).

On the other hand, with respect to the SDS-PAGE molecular weight standard low range (which includes phosphorylase B having 92,500, bovine serum albumin having 66,200, ovalbumin having 45,000, carbonic anhydrase having 31,000, soybean trypsin inhibitor having 21,500, and lysozyme having 14,400; available from Bio-Rad laboratories, U.S.A.), the same SDS-PAGE as mentioned above was conducted, to thereby obtain a molecular weight marker (lane 1 in FIG. 1) for estimating the respective molecular weights of proteins contained in the above-obtained reaction mixtures and the original sample solution, wherein the proteins had been separated in the same gel. With respect to the gel, silver staining was conducted using a Wako silver staining kit (available from Wako Pure Chemical Industries, Ltd, Japan), to thereby visualize proteins in the gel.

(4) Results

An SDS-PAGE pattern obtained in item (3) above is shown in FIG. 1. Lane 2 in FIG. 1 shows a separation pattern of proteins contained in the original sample solution containing streptolysin O, wherein the sample solution had been prepared in item (1) above and diluted 20-fold with PBS.

Lane 3 in FIG. 1 shows a separation pattern of proteins contained in the solution recovered from the cholesterol-immobilized microtiter plate. Lane 4 in FIG. 1 shows a separation pattern of proteins contained in the solution recovered from the microtiter plate having no cholesterol immobilized thereon.

From FIG. 1 it was confirmed that bands of molecular weights of 66,000 to 69,000 and 55,000 to 58,000, which are characteristic of streptolysin O, disappeared in lane 3. A hemolytic activity exhibited by the solution recovered from the cholesterol-immobilized microtiter plate was only 0.8%, based on the hemolytic activity exhibited by the sample solution.

The above results clearly indicate that, among proteins contained in the sample solution prepared in item 1, only streptolysin O having a biological activity was specifically bound to the cholesterol-immobilized carrier.

Example 2

Examination of reactivity of immobilized streptolysin O with antistreptolysin O antibody (1) Production of a Cholesterol-Immobilized Carrier 50 μl of an ethanol solution, containing cholesterol in a concentration of 20 μg/ml, was placed in each well of a microtiter plate (available from Sumitomo Bakelite Co., Ltd., Japan) and then, the plate was allowed to stand at 60° C. for 2 hours to evaporate and remove the solvent, to thereby prepare a cholesterol-immobilized microtiter plate. Skim milk (available from Snow Brand Milk Products Co., Ltd., Japan) was dissolved in 20 mM tris-hydrochloride buffer (pH 7.6, containing 0.14M sodium chloride) so that a 5 w/v % solution (hereinafter, frequently referred to as "blocking solution") was prepared. Subsequently, 100 μl of the blocking solution was placed in each well of the microtiter plate. Then, a reaction was allowed to proceed at room temperature for 2 hours. The wells were washed two times with 20 mM tris-hydrochloride buffer (pH 7.6, containing 0.14M sodium chloride) (hereinafter, frequently referred to as "washing solution"), to thereby prepare a cholesterol-immobilized carrier.

(2) Sensitization of Streptolysin O to a Cholesterol-Immobilized Carrier

The same sample solutions containing streptolysin O as prepared in Example 1, item (1) above were, respectively, diluted 100-fold, 400-fold, and 1,600-fold with 20 mM tris-hydrochloride buffer (pH 7.6, containing 0.14M sodium chloride) containing 0.5 w/v % skim milk (hereinafter, frequently referred to as "diluting solution"). 50 μl of each of the above-prepared dilutions and the above-mentioned diluting solution (as a control blank) was individually placed in each well of each of microtiter plates and then, a reaction was allowed to proceed at room temperature for 2 hours. Subsequently, the wells of each microtiter plate were washed 7 times with the washing solution, to thereby obtain microtiter plates to which streptolysin O was sensitized in predetermined amounts, and a control blank microtiter plate.

(3) Detection of an Immune Complex of Streptolysin O with Antistreptolysin O Antibody A standard solution containing antistreptolysin O antibody (131 IU/ml) (hereinafter, frequently referred to as "antistreptolysin O antibody standard solution") obtained from Japanese National Institute of Health was diluted 500-fold with the above-mentioned diluting solution, and 50 μl of the resultant dilution was placed in each well of each of the microtiter plates obtained in item (2) above and then, a reaction was allowed to proceed at room temperature for 1 hour. Subsequently, the wells of each microtiter plate were washed 7 times with the above-mentioned washing solution. Alkaline phosphatase-labeled goat F(ab')$_2$ antihuman IgG (available from Bio Source International, Inc.-Tago Products, U.S.A.) (enzyme-labeled secondary antibody) was diluted 1,000-fold with the diluting solution, and 50 μl of the resultant dilution was placed in each well of each microtiter plate. Then, a reaction was allowed to proceed at room temperature for 1 hour.

Subsequently, the wells of each microtiter plate were washed 7 times with the washing solution. 100 μl of a 0.5 mg/ml solution (substrates) of p-nitrophenyl phosphate (available from Wako Pure Chemical Industries, Ltd., Japan) in diethanolamine buffer (pH 9.5) was placed in each well. Then, a reaction was allowed to proceed at room temperature for 15 minutes, followed by adding 100 μl of 0.5N aqueous sodium hydroxide to each well to thereby terminate enzyme reaction. With respect to each solution taken from the wells, absorbances ($\Delta E$) at 405 nm were measured.

(4) Results

The results of detection of an immune complex of streptolysin O with antistreptolysin O antibody are shown in FIG. 2. FIG. 2 clearly indicates that streptolysin O immobilized on the carrier through cholesterol maintained a reactivity with antistreptolysin O antibody.

Example 3

Determination of antistreptolysin O antibody titer (1) Production of a Streptolysin O-Immobilized Carrier Polystyrene latex having a particle diameter of 0.12 μm (available from Sekisui Chemical Co., Ltd., Japan) was suspended in 10 v/v % aqueous ethanol so that a 2 w/v % polystyrene latex suspension was prepared. 1 part by volume of 10 v/v % aqueous ethanol containing cholesterol (available from Nakarai Chemical Ltd., Japan) in a concentration of 200 μg/ml was added to 1 part by volume of the above-prepared latex suspension, and contact therebetween was effected at room temperature for 2 hours.

To 1 part by volume of the resultant mixture were added 9 parts by volume of PBS containing 2 w/v % BSA and then, a reaction was allowed to proceed at room temperature for 2 hours. The resultant mixture was centrifuged at 12,000 r.p.m. for 20 minutes to thereby recover latex particles. The recovered latex particles were resuspended in PBS so that a 0.2 w/v % latex suspension was prepared. The sample solution containing streptolysin O, prepared in Example 1, item (1) above, was diluted 50-fold with PBS containing 0.4 w/v % BSA, and 1 part by volume of the resultant dilution was added to 1 part by volume of the latex suspension obtained above and then, a reaction was allowed to proceed at room temperature for 2 hours. Subsequently, the resultant mixture was centrifuged at 12,000 r.p.m. for 20 minutes to thereby recover latex particles. The recovered latex particles were resuspended in PBS so that a 0.1 w/v % latex suspension was prepared. Thus, streptolysin O-immobilized latex particles were obtained in the form of a suspension.

(2) Determination of the Antistreptolysin O Antibody Titer

600 μl of PBS and 200 μl of test serum were added to 200 μl of the streptolysin O-immobilized latex particle suspension prepared in item (1) above. Then, a reaction was allowed to proceed at 37° C. for 5 minutes, and an absorbance (ΔE) at 590 nm of the resultant reaction mixture was measured. An antistreptolysin O antibody titer was determined by referring to a calibration curve previously obtained by the method of the present invention using a standard solution containing antistreptolysin O antibody.

(3) Results

The calibration curve in FIG. 3 obtained by the method of the present invention illustrates the relationship between the antistreptolysin O antibody titer and the absorbance at 590 nm. From FIG. 3 it will be understood that a reliable calibration curve can be obtained by the method of the present invention. The relationship between the antistreptolysin O antibody titer determined by the method of the present invention and the antistreptolysin O antibody titer determined by the conventional Rantz-Randall method is shown in FIG. 4. FIG. 4 clearly indicates that the results obtained by the method of the present invention are well in agreement with those obtained by the Rantz-Randall method for determining antistreptolysin O antibody.

Example 4

Determination of antistreptolysin O antibody titer (1) Production of a Streptolysin O-Immobilized Carrier 50 μl of a 10 v/v % aqueous ethanol solution containing cholesterol (available from Nakarai Chemical Ltd., Japan) in a concentration of 100 μg/ml, was placed in each well of a microtiter plate (available from Sumitomo Bakelite Co., Ltd., Japan) and then, the plate was allowed to stand at room temperature for 2 hours, followed by washing the wells 2 times with purified water. Skim milk (available from Snow Brand Milk Products Co., Ltd., Japan) was dissolved in 20 mM tris-hydrochloride buffer (pH 7.6, containing 0.14M sodium chloride) so that a 5 w/v % solution (blocking solution) was prepared. Subsequently, 100 μl of the blocking solution was placed in each well of the microtiter plate prepared above. Then, a reaction was allowed to proceed at room temperature for 2 hours.

The above-mentioned wells were washed two times with 20 mM tris-hydrochloride buffer (pH 7.6, containing 0.14M sodium chloride) (washing solution). The sample solution containing streptolysin O as prepared in Example 1, item (1) above was diluted 1000-fold with 20 mM tris-hydrochloride buffer (pH 7.6, containing 0.14M sodium chloride) containing 0.5 w/v % skim milk (diluting solution). 50 μl of the above-prepared dilution was placed in each well and then, a reaction was allowed to proceed at room temperature for 2 hours. Subsequently, the wells were washed 7 times with the washing solution, to thereby prepare a streptolysin O-immobilized microtiter plate.

(2) Determination of an Antistreptolysin O Antibody Titer

An antistreptolysin O antibody titer was determined by utilizing BECKMAN Biomek 1000 Automated Laboratory Workstation (available from Beckman Instruments, Inc., U.S.A.). 50 μl of test serum diluted 100-fold with the above-mentioned diluting solution was placed in each well of the microtiter plate obtained in item (1) above and then, a reaction was allowed to proceed at room temperature for 1 hour. Subsequently, the wells were washed 7 times with the above-mentioned washing solution. 50 μl of a primary testing reagent [alkaline phosphatase-labeled goat F(ab')$_2$ antihuman IgG (available from Bio Source International, Inc.—Tago Products, U.S.A.) (enzyme-labeled secondary antibody) diluted 1,000-fold with the diluting solution] was placed in each well of the microtiter plate. Then, a reaction was allowed to proceed at room temperature for 1 hour. Subsequently, the wells were washed 7 times with the washing solution.

100 μl of a secondary testing reagent [a 0.5 mg/ml solution (substrate) of p-nitrophenyl phosphate (available from Wako Pure Chemical Industries, Ltd., Japan) in diethanolamine buffer (pH 9.5)] was placed in each well. Then, a reaction was allowed to proceed at room temperature for 15 minutes. 100 μl of 0.5N aqueous sodium hydroxide was added to each well, to thereby terminate the enzyme reaction. With respect to each reaction mixture taken from the wells, absorbances (ΔE) at 405 nm were measured. An antistreptolysin O antibody titer was determined by referring to a calibration curve previously obtained by the method of the present invention using a standard solution containing antistreptolysin O antibody.

(3) Results

The calibration curve in FIG. 5 obtained by the method of the present invention illustrates the relationship between the antistreptolysin O antibody titer and the absorbance at 405 nm. From FIG. 5 it will be understood that a reliable calibration curve can be obtained by the method of the present invention. The relationship between the antistreptolysin O antibody titer determined by the method of the present invention and the antistreptolysin O antibody titer determined by the conventional Rantz-Randall method is shown in FIG. 6. FIG. 6 clearly indicates that the results obtained by the method of the present invention are well in agreement with those obtained by the Rantz-Randall method for determining antistreptolysin O antibody.

What is claimed is:

1. A method for immunologically determining antistreptolysin O antibody, which comprises:

(a) contacting a test sample solution containing antistreptolysin O antibody with a binding agent capable of specifically binding said antistreptolysin O antibody thereto, thereby selectively binding said antistreptolysin O antibody to said binding agent by antigen-antibody reaction, and (b) determining an amount of said antistreptolysin O antibody bound to said binding agent, said binding agent comprising a streptolysin O-immobilized carrier obtained by contacting a solution containing streptolysin O with a carrier having immobilized thereon at least one steroid represented by formula (1):

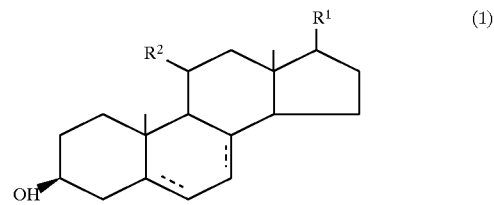

wherein $R^1$ is selected from the group consisting of a side chain moiety of cholesterol and a side chain moiety of cholic acid, wherein each of said side chain moieties is independently unsubstituted or substituted and independently saturated or unsaturated; $R^2$ is hydrogen or hydroxyl; and each dashed line independently represents a single bond or no bond, such that each dashed line and a solid line adjacent thereto together independently form a double bond or a single bond.

2. The method according to claim 1, wherein said immobilized steroid is present in an amount of from 0.025 nmol/cm$^2$ to 250 nmol/cm$^2$ with respect to the surface area of the carrier.

3. The method according to claim 1, wherein said immobilized steroid is present in an amount of from 0.25 nmol/cm$^2$ to 25 nmol/cm$^2$ with respect to the surface area of the carrier.

4. The method according to claim 1, wherein said immobilized streptolysin O is present in an amount of from 0.001 pmol/cm$^2$ to 1 nmol/cm$^2$ with respect to the surface area of the carrier.

5. The method according to claim 1, wherein said immobilized streptolysin O is present in an amount of from 0.01 pmol/cm$^2$ to 100 pmol/cm$^2$ with respect to the surface area of the carrier.

6. The method according to claim 1, wherein said immobilized steroid represented by formula (1) is cholesterol, 7-dehydrocholesterol, cholestanol, coprostanol, $\Delta^7$-cholestenol, $\Delta^7$-coprostenol, β-sitosterol, 7-dehydro-β-sitosterol, stigmasterol, 7-dehydrostigmasterol, campesterol, 7-dehydrocampesterol, stigmastanol, $\Delta^7$-stigmastenol, 11α-hydroxycholesterol, $\Delta^{22}$-stigmastenol, α-spinasterol, campestanol, $\Delta^7$-campestenol, 20α-hydroxycholesterol, brassicasterol, ergosterol, cerebrosterol, 7-dehydrocerebrosterol, cerebrostanol, $\Delta^7$-cerebrostenol, desmosterol, 7-dehydrodesmosterol, 3β-hydroxycholanic acid, or 3β-hydroxy-$\Delta^5$-cholenic acid.

7. The method according to claim 1, wherein said carrier is a colloidal particle, a bead, a ball, a microtiter plate, a test tube or a membrane.

8. The method according to claim 1, wherein step (b) is performed by at least one assay selected from the group consisting of immune agglutination assay, enzyme immunoassay, radioimmunoassay, fluoroimmunoassay, immunostaining, counting immunoassay, latex photometric immunoassay (LPIA) and nephelometric immunoassay (NIA).

* * * * *